United States Patent
Cammilli et al.

[11] Patent Number: 6,167,305
[45] Date of Patent: *Dec. 26, 2000

[54] IMPLANTABLE ELECTRIC HEART DEFIBRILLATION SYSTEM WITH ATTENUATION OF THE PAIN RESULTING FROM THE ELECTRIC SHOCK

[75] Inventors: Leonardo Cammilli, Via Caselli 11, I-50131 Firenze; Gino Grassi, Via Pasqui 31, I-50019 Sesto Fiorentino, Firenze, both of Italy

[73] Assignees: Leonardo Cammilli; Gino Grassi; Massimo Fossi, all of Florence, Italy

[*] Notice: This patent issued on a continued prosecution application filed under 37 CFR 1.53(d), and is subject to the twenty year patent term provisions of 35 U.S.C. 154(a)(2).

[21] Appl. No.: 09/057,206

[22] Filed: Apr. 8, 1998

[30] Foreign Application Priority Data

Apr. 8, 1997 [IT] Italy ................................ FI97A0071

[51] Int. Cl.[7] .......................................................... A61N 1/39
[52] U.S. Cl. .................................................... 607/5; 607/3
[58] Field of Search ................................ 607/3.5, 14, 46

[56] References Cited

U.S. PATENT DOCUMENTS

| | | |
|---|---|---|
| 4,360,026 | 11/1982 | Venin et al. . |
| 5,304,208 | 4/1994 | Inguaggiato et al. . |
| 5,662,689 | 9/1997 | Elsberry et al. . |
| 5,792,187 | 8/1998 | Adams ........................................ 607/5 |

FOREIGN PATENT DOCUMENTS

| | | |
|---|---|---|
| 0 253 505 A2 | 1/1988 | European Pat. Off. . |
| 0 410 954 A2 | 1/1991 | European Pat. Off. . |
| 0 515 319 | 11/1992 | European Pat. Off. . |
| 0 580 128 A2 | 1/1994 | European Pat. Off. . |
| 0 582 162 | 2/1994 | European Pat. Off. . |
| 0 599 588 A2 | 6/1994 | European Pat. Off. . |
| 0 655 260 | 5/1995 | European Pat. Off. . |
| 0 770 406 | 5/1997 | European Pat. Off. . |
| 0 778 049 | 6/1997 | European Pat. Off. . |
| WO 93/02746 | 2/1993 | WIPO . |
| WO 97/09088 | 3/1997 | WIPO . |

OTHER PUBLICATIONS

European Search Report; including abstract, dated Jun. 3, 1998, 3 pages.

*Primary Examiner*—George R. Evanisko
*Attorney, Agent, or Firm*—Popovich & Wiles PA

[57] ABSTRACT

An implantable electrical heart defibrillation system for both ventricle and atrium is proposed and is characterized in that it acts in a manner such as:

to diagnose the type of arrhythmia within a maximum time of 2 seconds from the onset of the arrhythmia;

to deliver the therapeutic shock by electrodes implanted in the region to be defibrillated no more than 4–5 seconds after the recognition of the arrhythmia, if it is ventricular fibrillation, so that the patient does not loose consciousness;

immediately after the onset of the arrhythmia and before the defibrillation shock is delivered, to prevent the conduction of neural pain signals coming from the region in which the electric shock acts, by nerve stimulation by a catheter inserted in the spinal column, utilizing the gate effect, or by the perfusion of a drug with immediate analgesic effect by an infusion pump and a catheter positioned in the region affected by the pain signals. This system enables defibrillation or conversion to be carried out with the patient conscious and within a sufficiently short time to be able to use low shock energy, and with prevention of the consequent painful shock. This considerably improves the quality of life of the patient who is no longer subject to loss of consciousness during ventricular fibrillation and does not feel the pain during the electric shock.

1 Claim, 4 Drawing Sheets

IMPLANTABLE ELECTRIC HEART DEFIBRILLATION SYSTEM WITH ATTENUATION OF THE PAIN RESULTING FROM THE ELECTRIC SHOCK

FIELD OF THE INVENTION

The present invention concerns a heart defibrillator and a method for its operation.

The invention has been developed with particular attention to its possible application to so-called heart defibrillators. The invention is, however applicable to defibrillators in generally and should not therefore be understood as limited to the specific field of use referred to below in the present description.

BACKGROUND OF THE INVENTION

Most sudden heart deaths are due to ventricular fibrillation in patients both with and without coronary disease. Ventricular fibrillation consists of chaotic, asynchronous and fractional activity of the ventricles. In a heart which has started the ventricular fibrillation process, all of the cells contract independently and not synchronously, with the final result that the pumping function of the heart is lost and circulatory arrest occurs; without intervention, the patient dies.

The only way of intervening is by electric heart defibrillation. This method, which was implemented successfully as early as 1908, came back into clinical practice around the 1940s and has been used increasingly since then. External defibrillation is achieved by applying to the patient's chest two plates by means of which an electric shock is transmitted. In recent years, implantable electric defibrillators have been designed and produced and these apply the electric shock directly to the heart wall, the shock being delivered automatically as soon as ventricular fibrillation is recognized by the circuits.

It should also be noted that malignant ventricular tachycardia (MVT), which is usually a precursor of ventricular fibrillation, can also be treated by electric cardioversion. A stimulation system with anti-tachycardia programs (with burst and premature extra-stimulation capabilities and the like) which are used as a first approach for the cardioversion of MVT is fitted, together with the defibrillation system, in the same device. In serious cases which are insensitive to anti-arrhythmic stimulation, when a certain number of attempts with this program have been found ineffective, the system can deliver an electric shock which has a greater probability of interrupting the MVT but which usually has less energy than for ventricular fibrillation.

The implantation of these devices (ICDs—implantable cardioverter defibrillators) started in 1980 and, since the 1990s, has increased notably because of the considerable technological progress and the increased ease of implantation due, in particular, to the use of catheter-electrodes which are introduced by a peripheral venous route in the same manner as for the implantation of pacemakers.

The implantation of ICDs is currently the only safe means of ensuring the survival of patients affected by these arrhythmias which are otherwise fatal.

There are, however, considerable problems, including:

a) the harmful nature of the electric shock which, with the energy of about 30 Joules currently used, damages the mitochondrial structures of the cells, and b) the fact that the life of the patient wearing the ICD is rendered traumatic by the loss of consciousness which occurs in the presence of ventricular fibrillation and hence of defibrillation, even though this saves the patient's life.

In fact, the shock is delivered about 10 seconds after ventricular fibrillation is recognized; this leads to circulatory arrest with loss of flow of oxygenated blood to the brain so that, after 5–6 seconds, the patient loses consciousness, falling to the ground if he is standing up.

The delay in the delivery of the shock is necessary in order to confirm the diagnosis of ventricular fibrillation and to charge the capacitor which serves to store the energy for the delivery of the shock.

The delay is also necessary in order to deliver the shock when the patient is unconscious so that he does not feel the pain of the discharge. In some cases of younger patients who are still conscious when the discharge is delivered, the sensation of pain is in fact so strong and distressing that some patients have asked for the ICD to be removed.

The situation in which it is necessary to interrupt MVT by means of the shock should also be considered; in fact the delivery of the shock takes place when the patient is fully conscious since, although MVT is disabling, it does not cause loss of consciousness. In these cases, the pain complained of by the patient which, amongst other things, is sudden, is very great, although it is not of long duration.

In any case, even in patients who do not feel the shock, their existence becomes so traumatic with the continual fear and expectation of crises accompanied by loss of consciousness that they sometimes prefer the risk of death.

A condition which is similar to ventricular fibrillation as a physiological phenomenon, although it does not involve an immediate danger of death of the patient will now also be considered.

Atrial fibrillation (AF) is an arrhythmia which causes disappearance of the atrial contractions which are replaced by fibrillation, that is, by uncoordinated activity which nullifies the pumping effect of normal contraction. It is compatible with life since blood circulation is maintained, although with a reduction of the cardiac blood flow.

However, atrial fibrillation causes stagnation of the blood in the atrium which favors the formation of a thromboembolism which, in time, puts the patient's life at risk. Moreover, the irregularity of the ventricular response may set off dangerous ventricular tachycardia. This arrhythmia can be treated pharmacologically but insensitivity to the drugs is often encountered.

Another possibility is electric cardioversion which consists of the application of an electric shock similar to ventricular defibrillation but with lower discharge energy. A couple of years ago, the implanted atrial defibrillator technique was proposed and implemented in order to deliver a shock directly to the appropriate locations of the heart cavity at the onset of the arrhythmia. For this treatment, the need to attenuate or cancel out the pain caused by the discharge which, in this case, is applied to conscious patients who have difficulty in tolerating it, becomes fundamental.

It can be seen from the foregoing description that an ability to prevent the pain signals from being perceived by the patient is very important.

SUMMARY OF THE INVENTION

The object of the invention is to produce an implantable atrial or ventricular defibrillator which allows patients to have a less traumatic life, by means of the characteristics which will be described below.

In one aspect, this invention is a method of electrically defibrillating a heart, comprising sensing a heart arrhythmia;

stimulating the spinal column to produce an analgesic effect; and delivering an electrical shock to defibrillate the heart. The method may also include stimulating the spinal column by saturating the pathways of the pain caused by the shock by the "gate control" method. Preferably, the step of delivering the electrical shock is synchronized with the patient's QRS. A blanking circuit also may be provided. The blanking circuit generates a signal which can protect the other circuits from the electrical shock, and is activated prior to the delivery of the shock and terminated after delivery of the shock. The arrhythmia may be a ventricular fibrillation or atrial arrhythmia.

The step of sensing the arrhythmia may include sensing within 2 seconds from the start of the arrhythmia an electrical signal from the heart having an average frequency greater than 280–300 beats per minute with irregularities in period and amplitude and sensing a stoppage of pumping of the heart.

The step of delivering the electrical shock may include delivering the electrical shock no longer than three seconds after sensing the arrhythmia. The step of stimulating the spinal column to produce an analgesic effect may include infusing an analgesic drug or electrically stimulating a nerve immediately upon sensing the arrhythmia.

The step of sensing the arrhythmia preferably allows sufficient time to verify the stability of the arrhythmia. The step of delivering the electrical shock may take up to one minute from sensing the arrhythmia, and the electrical shock may be between 1 and 10 Joules. The step of stimulating the spinal column preferably occurs at least two seconds before the electrical shock.

Alternatively, the arrhythmia may be ventricular tachycardia. The step of sensing the arrhythmia may include sensing an electrical signal from the heart beating up to 300 beats per minutes, wherein the beats have substantially constant frequency and amplitude, and further sensing an attenuated and/or irregular blood flow without stoppage of the heart. A pacing electrical stimulus may be applied as a first treatment and, if this is unsuccessful after a programmed number of attempts, a low energy cardioversion shock may be delivered.

The step of stimulating the spinal column may include infusing an analgesic drug with immediate effect. The step of sensing the arrhythmia may include sensing the arrhythmia through electrical, mechanical, and electromechanical impulses.

DETAILED DESCRIPTION OF THE PREFERRED EMBODIMENTS

First of all, the case of ventricular fibrillation will be considered; the following solutions are proposed:

a) to make a sure diagnosis within the first 1–2 seconds from the start of the arrhythmia, b) to deliver the electric shock no more than 3–4 seconds after the recognition of the ventricular fibrillation so as to start the shock when the patient is conscious and with less energy than is currently used because of the earliness of the intervention, and c) in order to be able to operate as in b), to prevent the patient's nervous system from receiving the pain stimulus due to the electric shock and to the abrupt contraction of the adjacent muscles.

This can be achieved, for example, by the insertion of electrodes in the spinal column, the electrodes being connected to a neural stimulator which will saturate the pain-conduction pathways (gate effect), preventing the pain from being perceived by the patient or, in any case, causing it to arrive greatly attenuated. The same result can also be achieved, for example, by means of an infusion pump which can send a drug which has an immediate effect (e.g. a recently investigated drug, conopeptide, with effectiveness 100 times greater than morphine) to the appropriate sites of the nerve endings affected by the shock in order to cancel out the perception of the pain.

The instrument for implementing the system proposed is made up essentially as shown by the simplified block diagram which shows its main components.

Figure 1:
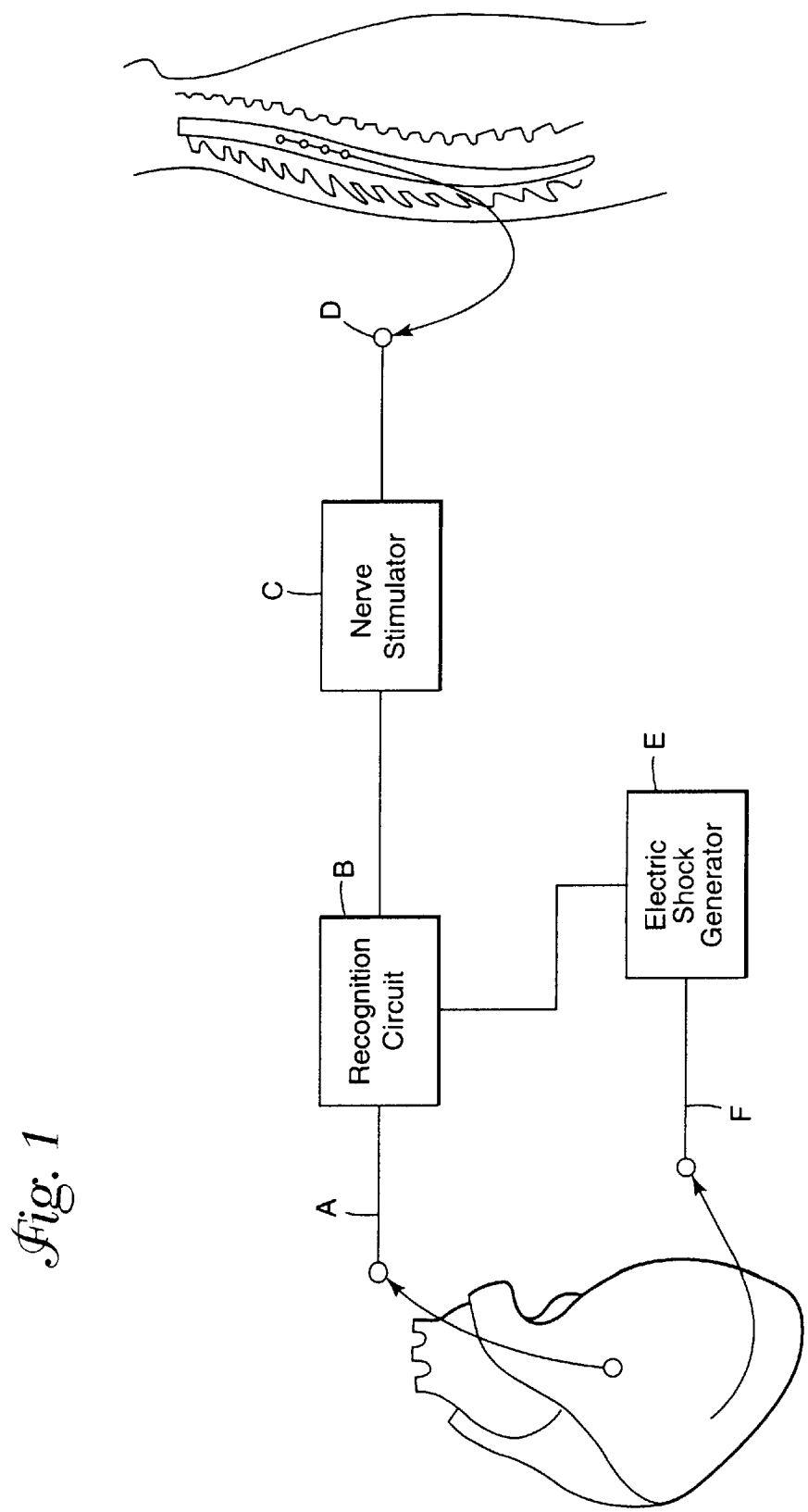
FIG. 1 is a block diagram showing the elements of the defibrillating system

In FIG. 1, the various blocks represent:

A sensors for detecting fibrillation,

B fibrillation or tachycardia recognition circuit,

C programmable neural stimulator or analgesic drug infusion pump,

D neural electrode system for the spinal column, or catheter for the infusion of the analgesic drug, E quickly set electric-shock generator, and F defibrillation electronic system.

The sequence of operation is as follows. The circuit B recognizes the presence of fibrillation by means of the sensors A within a time no longer than 2 sec. When recognition has taken place, a signal starts the neural stimulator (or the infusion pump) C which produces the gate effect in the nervous system involved in receiving the expected pain signals, by means of the spinal electrodes (or the infusion catheter) D. At the same time, the quick shock-energy generator E charges the capacitor which stores the energy within a time less than or equal to 3 sec. If the circuit B confirms fibrillation, the discharge is delivered at a time no longer than 4–5 sec. after recognition.

The solutions set out in points a), b) and c) described above are thus achieved:

quick recognition of ventricular fibrillation;

immediate saturation of the pain-conduction pathways; and defibrillation at times close to the onset of the arrhythmia, within the first 5 seconds.

The various components of the proposed system can be formed by solutions already existing in various implantable defibrillator models and spinal-chord nerve stimulators (or drug infusers) which have already been produced.

The detection of ventricular fibrillation with regard to its electrical component has now been established and it is proposed herein to supplement it by means of a second sensor, for example, a mechanical sensor so as to be able to recognize the type of arrhythmia with certainty within a very short time. The parameters of neural stimulators, which are generally used to treat long-term pains, have to be adapted to the need to prevent the propagation of a pain which is expected, sudden and of short duration, at least with regard to its cause. Any infuser must be designed to deliver an analgesic drug with immediate effect. The generator and supplier of the electric shock must be put into operation in a very short time as is, however, already provided for in the latest generations of defibrillators. Naturally, the entire device which forms the proposed system can preferably be fitted in a single implantable container although this is not functionally necessary as long as the various functions are interconnected electrically or electromagnetically.

Figure 2:
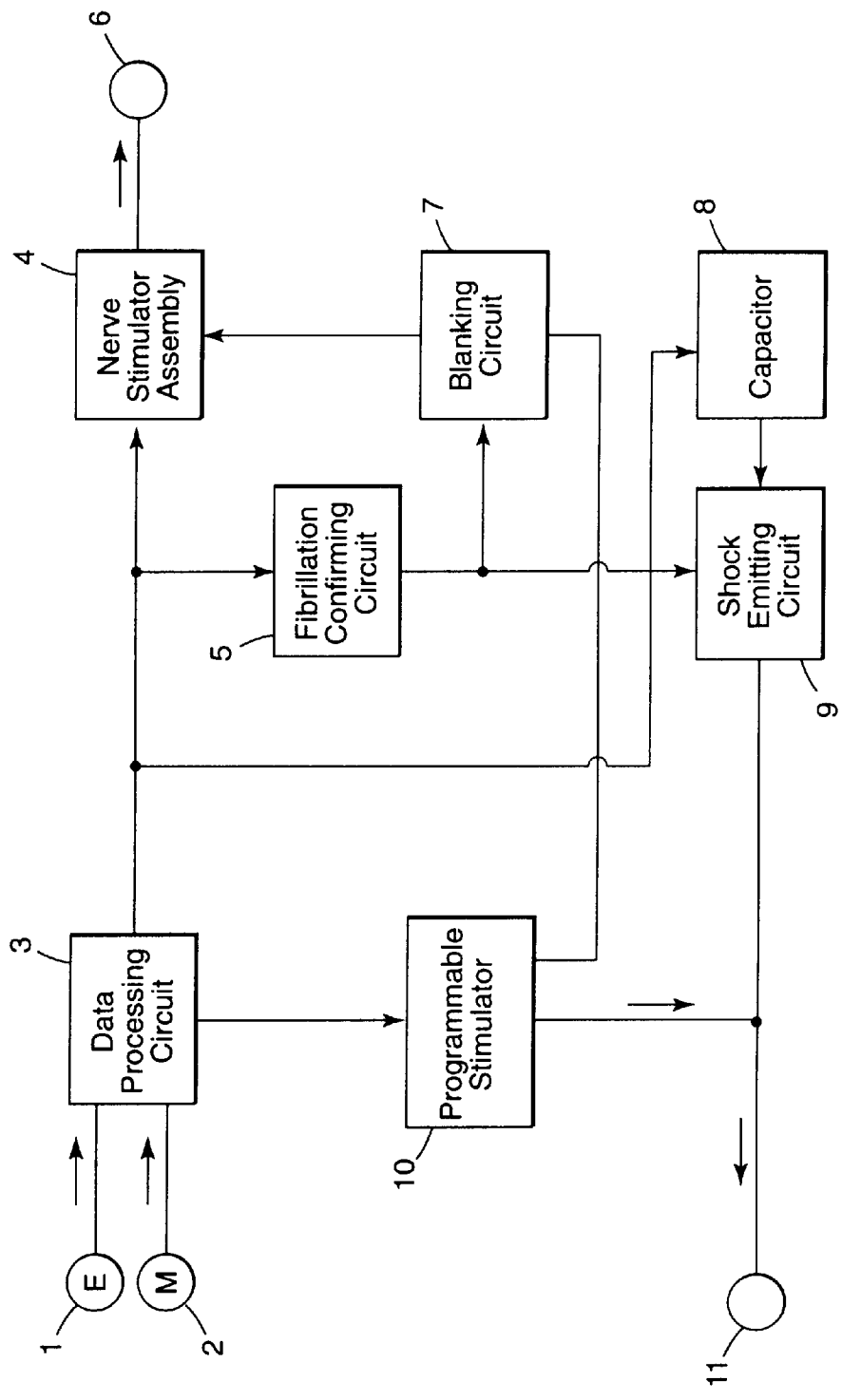
FIG. 2 is a block diagram describing an embodiment of the system in greater detail.

The block diagram of FIG. 2 will be considered in order to describe a possible embodiment of the system in greater detail. The sensors 1 and 2 constitute the arrhythmia detection and recognition system. The electric sensor 1 analyses the electrical signal of the heart which enables the presence of ventricular tachycardia to be distinguished from ventricular fibrillation, by considering, for example, the frequency of the complexes and the regularity of the period and amplitude of the heart signals. The electrical diagnoses which, in some cases, could be uncertain, can be confirmed with the use of a mechanical (or electromechanical) signal, for measuring, for example, systolic pressure, which is practically zero in ventricular fibrillation, or contractility, which is easily detectable by means of recently-proposed implantable transducers, or by rheography, or heart noise. Reference may be made, for example, to the documents EP-A-0 515 319, EP-A-0 582 162, EP-A-0 655 260, EP-A-0 770 406 and EP-A-0 778 049.

The algorithm which can be implemented with systems of this type enables ventricular tachycardia to be distinguished from ventricular fibrillation; in fact in ventricular tachycardia, neither the pressure nor the contractility become zero, although their values are much lower than the normal sinus rhythm and amplitude and frequency may be irregular; with ventricular fibrillation, on the other hand, the pressure and contractility fall practically and abruptly to zero and the heart noise is almost non-existent.

The circuit represented by block 3 is provided for processing the data obtained by 1 and 2 by an algorithm which, as stated above, recognizes the type of arrhythmia, providing a signal indicating the presence of ventricular fibrillation or ventricular tachycardia to downstream circuits. If the arrhythmia recognized is ventricular fibrillation the proposed system starts block 4 and block 8 together.

In this embodiment, block 4 represents, by way of non-limiting example, the nerve stimulator assembly the stimulating electrodes 6 of which are inserted in the spinal chord in positions in which the closure of the gate will block the transmission of the pain signals coming from the heart region and from the surrounding muscles. The drug infuser may be used in similar manner. The functional characteristics of block 4 are known to experts in the art and are programmed in a manner such that the neural stimulation effect is immediate (usually from 0.5 to 1 sec. delay) and effective for the region affected.

Block 8 represents the system for the storage of the shock energy, which consists in charging a capacitor such as that normally used in ICDs, contained in block 9. The main characteristic of block 8 is that it can charge the capacitor, which usually has a capacitance of between 80 and 180 $\mu$F, to the maximum energy of 25–30 J within a time less than or equal to 3 seconds. The short charging time is important for the purposes of the invention; it has already been achieved in the design of implantable defibrillators currently in production.

The circuit 5 confirms the presence of ventricular fibrillation about 4–5 seconds after the recognition effected by 3.

In this case, the circuit of block 9 provides for the emission of a shock with the electrical characteristics (wave-form, duration, etc.) required and programmed by the operator. The shock is delivered by means of the electrode system (endocavitary or epicardial) 11 which comprises the defibrillation electrodes and those for the pre-selected programmed stimulation for any ventricular tachycardia.

In fact, if the arrhythmia is recognized as ventricular tachycardia, a signal is sent to block 10 which comprises a programmable anti-tachycardia stimulator which can deliver the pre-selected stimulation program for tachyarrhythmia and implement the algorithms normally used for this treatment such as, for example, burst, premature extra-stimuli, overdrive. Block 10 is also capable of delivering a normal stimulation in the event of stoppage or asystole after defibrillation or cardioversion so as to promote the re-establishment of a possible sinus rhythm. The programmed stimulation is delivered by means of the electrode system 11.

Block 7 consists of a circuit provided for creating blanking which electrically excludes both the anti-arrhythmic pacemaker 10 and the neural stimulator 4 from normal operation in order, as far as possible, to protect the electronic circuits from the shock of the defibrillation signal which could damage them because of its high energy. The blanking signal is applied for a time slightly greater than the total duration of the shock pulse; a duration of about 20–30 mseconds, starting from the leading edge of the shock itself or a few mseconds earlier, will normally suffice. For the same reason and as is normally the case, the electrode systems 1, 2 and 6 must be protected from discharges greater than about 20 Volts, for example, by means of semiconductor devices well known in electronics.

The system proposed up to now can also be used with a few modifications in the case of atrial fibrillations. In this case, there is no need for early intervention, since this arrhythmia is disabling but not fatal. It is, however, important to try to prevent the painful sensation caused by the electric shock since this will take place when the patient is conscious. In the case of atrial cardioversion, the difference factors also render the production of the cardioverter easier and less critical. The energy required for atrial cardioversion is much lower than that required for ventricular defibrillation; normally from 1 to 10 Joules suffices. The charging of the capacitor for the shock can take place in a longer time, thus requiring a lower charge-generator power. To prevent pro-arrhythmic effects which could lead to ventricular fibrillation owing to the delivery of the shock in the period of ventricular vulnerability, the shock is synchronized with the patient's QRS.

Figure 3:
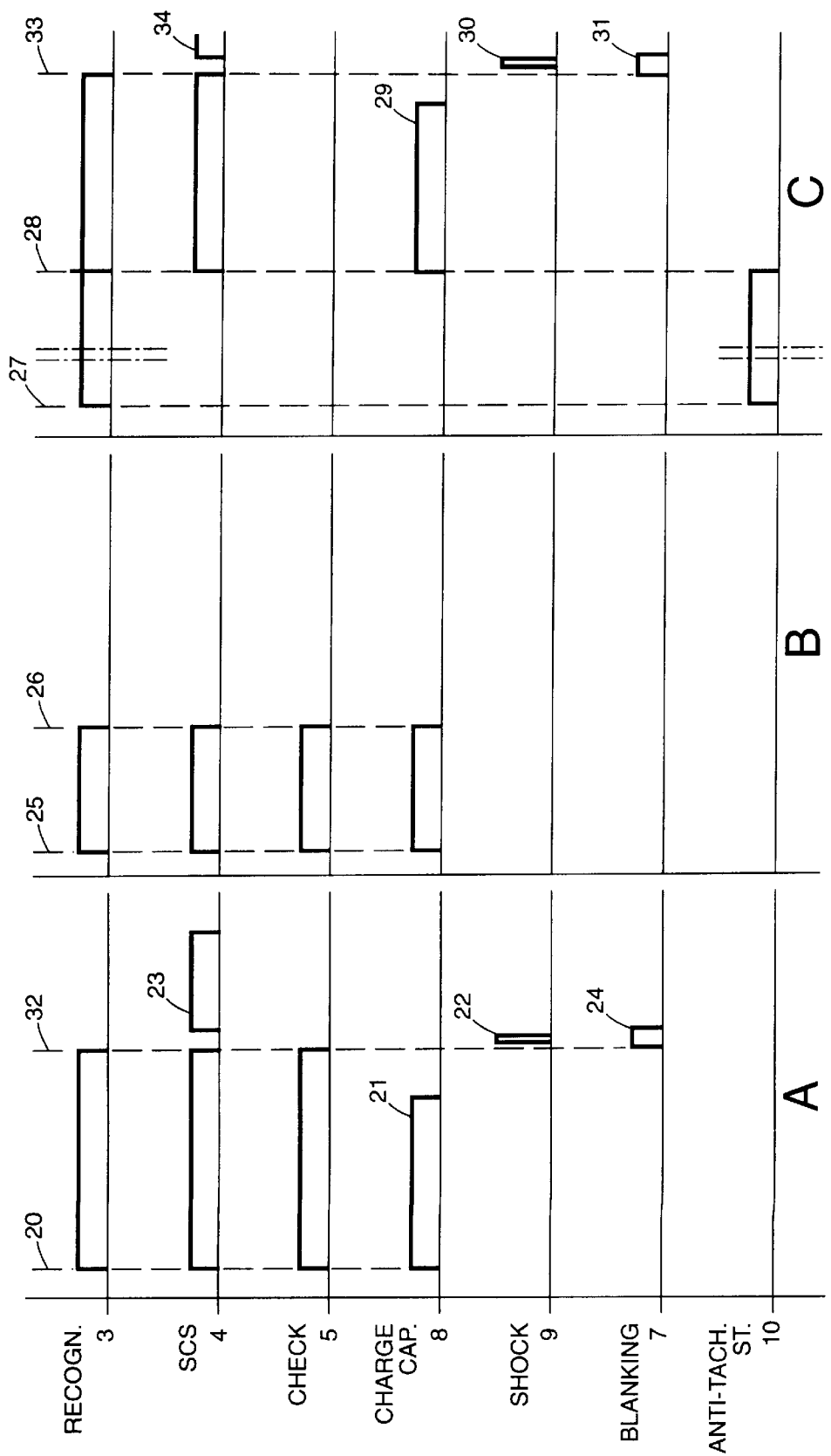
FIG. 3 illustrates the time sequences of the interventions for ventricular fibrillation of the various components which are characteristic of the proposed system.

In view of the similarities between the two defibrillation methods, it is thus possible to design a single device which can be programmed with the two different algorithms, the sole change in the hardware being in the electrode system 11 of FIG. 2. The time sequences of the interventions of the various components which are characteristic of the proposed system are shown schematically in FIG. 3 for ventricular fibrillation and in FIG. 4 for atrial fibrillation.

FIG. 3A describes operation during persistent ventricular fibrillation. Recognition system 3 notices the ventricular fibrillation at time 20 and immediately starts neural stimulator 4 and the charging of capacitor 8. At the same time, checking system 5 checks that arrhythmia is present. Capacitor 8 will already be charged at time 21. At time 32 programmed for the emission of the shock, blanking circuit 7 protects the circuits with a signal of duration 24 which is greater than discharge time 22, stimulator 4 also being prevented for the period 23. Immediately afterwards, circuit 9 delivers shock 22 which should interrupt the ventricular fibrillation. Neural stimulator 4 will continue to protect the patient from the pain for a programmable period which may be as long as a few minutes.

FIG. 3B shows a case of ventricular fibrillation which disappears naturally at a time earlier than that programmed for the discharge. After the start at time 25 which triggers stimulator 4 and charging circuit 8, the ventricular fibrillation disappears at time 26, and all of the circuits are reset.

FIG. 3C gives an example in which ventricular tachycardia occurs. At time 27, circuit 3 recognizes the type of arrhythmia as ventricular tachycardia and activates anti-arrhythmic stimulator circuit 10 which starts to deliver stimuli in accordance with the programmed algorithms.

If these stimuli are effective, the ventricular tachycardia will be stopped and circuits 3 and 10 will be reset. If, however, the treatment with anti-arrhythmic stimulator circuit 10 is not effective, after the delivery of a certain number of programs (3–5 times in succession) circuit 3 will start both neural stimulator generator 4 and the capacitor-charging circuit 8 at time 28 up to the time at which the programmed energy 25 is reached. At the time 33, as in the case described in FIG. 3A, blanking signal 31 will start and will protect the circuits of the system during the shock for period 34. The delivery of shock 30 will stop the arrhythmia and the system will be reset.

Figure 4:
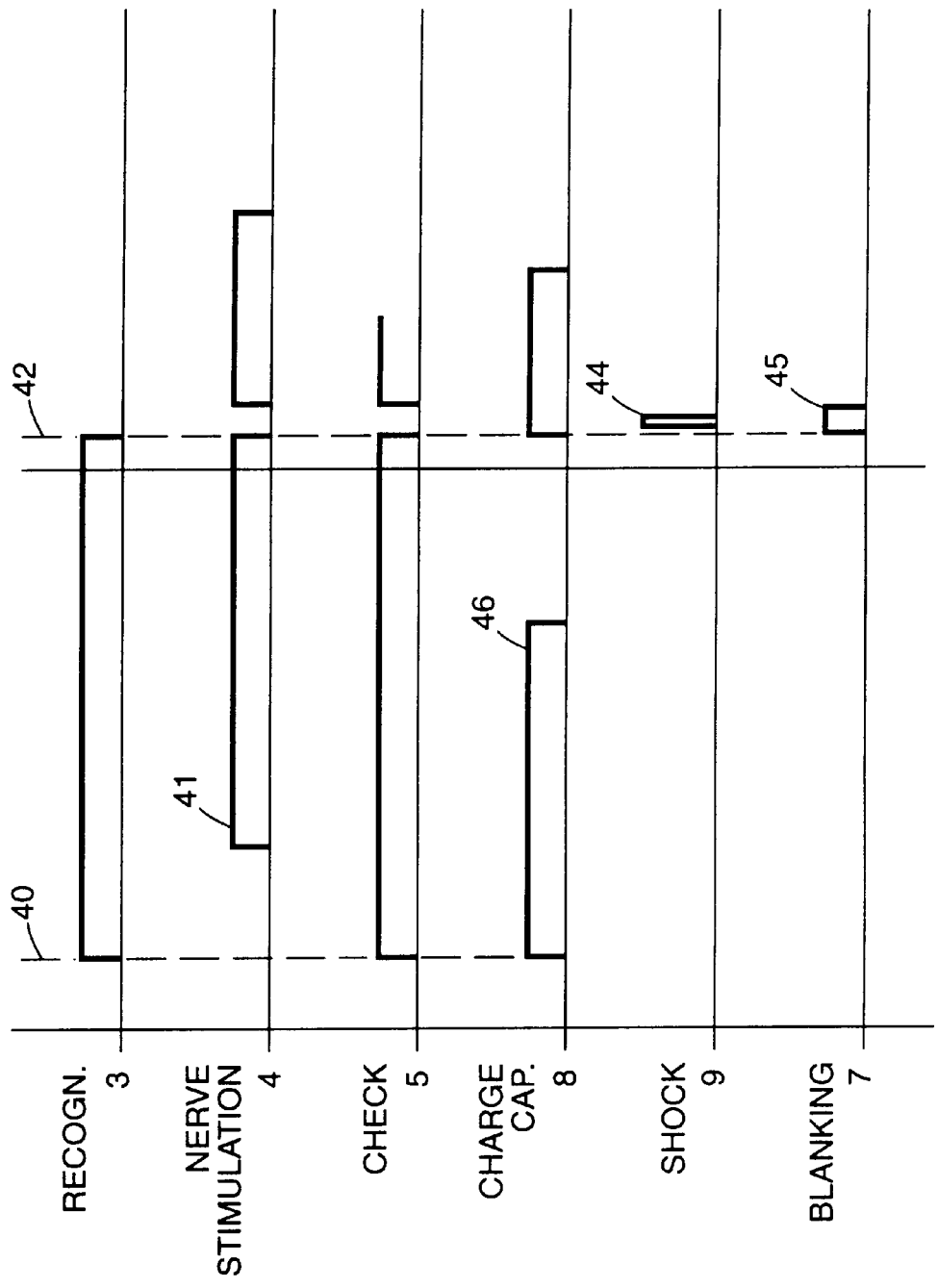
FIG. 4 illustrates the time sequences of the interventions for atrial fibrillation of the various components which are characteristic of the proposed system.

FIG. 4 shows the sequence of operation of the various blocks in the case of atrial fibrillation. Also this refers to FIG. 2.

Recognition system 3 detects atrial fibrillation at time 40. At the same time, the charging of the capacitor by block 8 is started, the programmed energy being reached after time 46 which may even be one minute. At the same time, or at time 41 after the recognition of the atrial fibrillation, neural stimulator 4 starts the stimulation. Checking system 5 checks the existence of atrial fibrillation.

At time 42, a fraction of a second before the shock, the blocking of the blanking unit is switched on for time 45 which lasts until a few hundred milliseconds after the shock. During time 45, the circuits of blocks 3, 4 and 5 are prevented and/or protected against the shock energy which is propagated through the patient's body. During time 45, the cardioversion electric shock is delivered and is synchronized with the patient's QRS by blocks 3 and 5. Circuits 3 and 5 then become active again in order to monitor the patient and neural stimulator 4 continues in accordance with the program setting.

What is claimed is:

1. A method of electrically defibrillating a heart, comprising:

(a) sensing a ventricular fibrillation;

(b) stimulating the spinal column to produce an analgesic effect; and (c) delivering an electrical shock to defibrillate the heart, wherein the step of sensing the ventricular fibrillation comprises sensing within 2 seconds from the start of the ventricular fibrillation an electrical signal from the heart having an average frequency of greater than 280 beats per minute and sensing a stoppage of pumping of the heart.

* * * * *